United States Patent
Schmelzer et al.

(10) Patent No.: US 9,238,031 B2
(45) Date of Patent: Jan. 19, 2016

(54) PROPELLANT-FREE AEROSOL FORMULATION FOR INHALATION

(71) Applicant: Boehringer Ingelheim International GmbH, Ingelheim am Rhein (DE)

(72) Inventors: Christel Schmelzer, Ingelheim am Rhein (DE); Franz-Rainer Weitzel, Schwabenheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/087,361

(22) Filed: Nov. 22, 2013

(65) Prior Publication Data

US 2014/0228397 A1    Aug. 14, 2014

Related U.S. Application Data

(63) Continuation of application No. 12/299,535, filed as application No. PCT/EP2007/054490 on May 9, 2007.

(30) Foreign Application Priority Data

May 19, 2006  (EP) .................................... 06114260
Jul. 28, 2006  (EP) .................................... 06118115

(51) Int. Cl.
| | | |
|---|---|---|
| A61K 31/44 | (2006.01) | |
| A61K 31/135 | (2006.01) | |
| A61K 31/46 | (2006.01) | |
| A61K 9/00 | (2006.01) | |
| A61K 31/137 | (2006.01) | |
| A61K 47/10 | (2006.01) | |
| A61K 47/18 | (2006.01) | |

(52) U.S. Cl.
CPC .............. *A61K 31/46* (2013.01); *A61K 9/0073* (2013.01); *A61K 9/0078* (2013.01); *A61K 31/137* (2013.01); *A61K 47/10* (2013.01); *A61K 47/183* (2013.01); *A61K 47/186* (2013.01)

(58) Field of Classification Search
None
See application file for complete search history.

(56) References Cited

U.S. PATENT DOCUMENTS

| | | |
|---|---|---|
| 6,176,442 B1 | 1/2001 | Eicher et al. |
| 7,470,422 B2 | 12/2008 | Freund et al. |
| 2001/0008632 A1* | 7/2001 | Freund et al. .................. 424/400 |
| 2003/0191151 A1* | 10/2003 | Chaudry et al. .............. 514/304 |
| 2006/0035874 A1 | 2/2006 | Lulla et al. |
| 2009/0185983 A1 | 7/2009 | Freund et al. |
| 2010/0056559 A1 | 3/2010 | Schmelzer et al. |
| 2010/0144784 A1 | 6/2010 | Schmelzer et al. |

FOREIGN PATENT DOCUMENTS

| | | |
|---|---|---|
| DE | 19653969 A1 | 6/1998 |
| WO | 9114468 A1 | 10/1991 |
| WO | 9407607 A1 | 4/1994 |
| WO | 9712683 A1 | 4/1997 |
| WO | 9712687 A1 | 4/1997 |
| WO | 9720590 A1 | 6/1997 |
| WO | 9827959 A2 | 7/1998 |
| WO | 9916530 A1 | 4/1999 |
| WO | 0113885 A1 | 3/2001 |
| WO | 03037159 A2 | 5/2003 |
| WO | 03037259 A2 | 5/2003 |
| WO | 2006027595 A1 | 3/2006 |
| WO | 2006037948 A2 | 4/2006 |
| WO | 2007134965 A1 | 11/2007 |
| WO | 2007134967 A1 | 11/2007 |

OTHER PUBLICATIONS

Beasley R et al: "Preservatives in Nebulizer solutions: Risks without Benefit" Pharmacotherapy, Boston, US, Bd. 18, Nr. 1, Jan. 1998.
International Search Report and Written Opinion for PCT/EP2007/054488 mailed Jul. 18, 2007.
International Search Report and Written Opinion for PCT/EP2007/054490 mailed Jul. 17, 2007.

* cited by examiner

*Primary Examiner* — Sreeni Padmanabhan
*Assistant Examiner* — Jody Karol
(74) *Attorney, Agent, or Firm* — Michael P. Morris; Atabak R. Royaee

(57) ABSTRACT

The present invention relates to propellant-free aerosol formulations for inhalation containing ipratropium bromide and salbutamol.

**10 Claims, No Dr

PROPELLANT-FREE AEROSOL FORMULATION FOR INHALATION

CROSS-REFERENCE TO RELATED APPLICATIONS

This application is a continuation application of U.S. patent application Ser. No. 12/299,535, filed on Aug. 3, 2009, which is a national stage entry of PCT/EP07/54490, filed on May 9, 2007, which claims priority to EP Patent Application No. 06114260.0, filed on May 19, 2006 and EP Patent Application No. 06118115.2, filed on Jul. 28, 2006, the entire content and disclosure of each of which is incorporated herein by reference.

The present invention relates to propellant-free aerosol formulations for inhalation containing ipratropium bromide and salbutamol.

DETAILED DESCRIPTION OF THE INVENTION

The present invention relates to propellant-free solution formulations for inhalation which contain the active substances salbutamol, optionally in the form of the pharmacologically acceptable acid addition salts thereof, and ipratropium bromide and optionally further excipients in a solvent selected from among water, ethanol and water-ethanol mixtures, while the weight ratio of salbutamol to ipratropium bromide is in the range from 5:1 to 5.5:1.

The solution formulations according to the invention do not contain any other active substances besides salbutamol and ipratropium bromide.

The weight ratio of salbutamol/ipratropium bromide is based on the ratio by mass of salbutamol contained in the solution formulation to ipratropium bromide contained in the solution.

The salbutamol is preferably contained in the formulations according to the invention in the form of one of the acid addition salts thereof with pharmacologically acceptable acids. Preferred acid addition salts of salbutamol are selected from the salts of hydrochloric acid, hydrobromic acid, nitric acid, sulphuric acid and phosphoric acid. Particularly preferably according to the invention, the salbutamol is used in the formulations according to the invention in the form of the sulphuric acid addition salt thereof. This acid addition salt is optionally also referred to within the scope of the present invention as salbutamol sulphate. The ipratropium bromide may be used in the preparation of the formulations according to the invention in anhydrous form or also in the form of one of its hydrates, preferably in the form of its monohydrate.

The medicament formulations according to the invention contain as solvent pure water, pure ethanol or mixtures of ethanol and water. If ethanol-water mixtures are used, the percentage content of ethanol by mass in these mixtures is preferably in the range between 5 and 99% ethanol, particularly preferably in the range from 10 to 96% ethanol. Most particularly preferred medicament formulations for the purposes of the present invention contain as solvent pure water, pure ethanol or ethanol-water mixtures containing between 50 and 92%, particularly preferably between 69 and 91% ethanol.

Optionally other cosolvents may be used besides ethanol and water. They are preferably selected from among the alcohols or ethers, such as for example isopropanol or tetrahydrofuran. However, according to the invention preferably no other solvent is used.

Particularly preferred medicament formulations according to the invention contain only water as solvent.

Normally, the formulations according to the invention contain pharmacologically acceptable acids to adjust the pH. The pH of the formulation according to the invention is preferably in the range from 3.0 and 4.0, preferably between 3.1 and 3.7, particularly preferably between 3.3 and 3.5 according to the invention. Particularly preferred solution formulations have a pH of 3.4.

Pharmacologically acceptable acids used to adjust the pH may be inorganic acids or organic acids. Examples of preferred inorganic acids are selected from the group consisting of hydrochloric acid, hydrobromic acid, nitric acid, sulphuric acid and phosphoric acid. Examples of particularly suitable organic acids are selected from the group consisting of ascorbic acid, citric acid, malic acid, tartaric acid, maleic acid, succinic acid, fumaric acid, acetic acid, formic acid and propionic acid. Preferred inorganic acids are hydrochloric acid and sulphuric acid, of which hydrochloric acid is particularly preferred according to the invention. Of the organic acids, ascorbic acid, fumaric acid and citric acid are preferred, while citric acid is particularly preferred according to the invention. If desired, mixtures of the abovementioned acids may also be used, particularly in the case of acids which have other properties in addition to their acidifying properties, e.g. those which act as flavourings or antioxidants, such as for example citric acid or ascorbic acid.

If desired, pharmacologically acceptable bases may be used to titrate the pH precisely. Suitable bases include for example alkali metal hydroxides and alkali metal carbonates. The preferred alkali metal ion is sodium. If bases of this kind are used, care must be taken to ensure that the resulting salts, which are then contained in the finished pharmaceutical formulation, are pharmacologically compatible with the abovementioned acid.

Examples of further excipients, which may optionally also be present in the solutions according to the invention in addition to the active substances salbutamol and ipratropium bromide, are particularly and preferably preservatives and complexing agents according to the invention.

By complexing agents are meant within the scope of the present invention molecules which are capable of entering into complex bonds. Preferably, these compounds should have the effect of complexing cations, most preferably metal cations. The formulations according to the invention preferably contain editic acid (EDTA) or one of the known salts thereof, e.g. sodium EDTA or disodium EDTA. Preferably, disodium edetate is used, optionally in the form of its hydrates, particularly preferably in the form of its dihydrate. If disodium edetate is used as complexing agent within the scope of the formulations according to the invention, the content of disodium edetate is preferably in the range from 0 to 100 mg pro 100 g, particularly preferably in the range from 5 to 70 mg per 100 g of the formulation according to the invention. Preferably, the formulations according to the invention contain a complexing agent, particularly preferably disodium edetate in an amount of about 40 to 60 mg per 100 g, particularly preferably about 45 to 55 mg per 100 g, particularly preferably 50 mg per 100 g of the formulation according to the invention. Of equal importance according to the invention are formulations which contain the complexing agent in an amount of about 7 to 12 mg per 100 g, particularly preferably about 10 mg per 100 g of the formulation according to the invention.

Also of equal importance according to the invention are formulations which contain the complexing agent in an amount of about 3 to 7 mg per 100 g, particularly preferably about 5 mg per 100 g of the formulation according to the invention.

Preservatives may be used to protect the formulation from contamination with pathogens. Suitable preservatives are those which are known in the art, particularly benzalkonium chloride, cetyl pyridinium chloride or benzoic acid or benzoates such as sodium benzoate in the concentrations known from the prior art. Preferably benzalkonium chloride is added to the formulation according to the invention. The amount of benzalkonium chloride is between 1 mg and 50 mg per 100 g formulation, preferably about 2 to 15 mg per 100 g, particularly preferably about 3 to 12 mg per 100 g, particularly preferably about 10 mg per 100 g of the formulation according to the invention. Benzalkonium chloride may also be used according to the invention in admixture with other preservatives.

In the formulations according to the invention ipratropium bromide is usually present in an amount of from 125-200 mg per 100 g solution. Preferably the formulations according to the invention contain the active substance ipratropium bromide in an amount of 150-190 mg per 100 g solution, particularly preferably in an amount of 160-180 mg per 100 g solution. The skilled man will easily be able to calculate from these figures the corresponding amounts of ipratropium bromide-monohydrate which are particularly preferably used according to the invention.

Particularly preferred formulations according to the invention contain besides the above-mentioned amounts of ipratropium bromide an amount of salbutamol such that the weight ratio of salbutamol to ipratropium bromide is in the range from 5.1:1 to 5.4:1. In particularly preferred formulations according to the invention the weight ratio of salbutamol to ipratropium bromide is in the range from 5.2:1 to 5.3:1.

Particularly preferred formulations according to the invention contain 160-190 mg, preferably 170 to 180 mg ipratropium bromide-monohydrate and 900-1200 mg, preferably 1000-1100 mg salbutamol sulphate per 100 g solution.

In another aspect the present invention relates to the use of the above-mentioned medicament formulations according to the invention for preparing a medicament for the treatment of respiratory complaints selected from the group comprising obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

Preferably, the medicament formulations according to the invention are used to prepare a medicament for the treatment of obstructive pulmonary diseases selected from the group consisting of bronchial asthma, pediatric asthma, severe asthma, acute asthma attacks, chronic bronchitis and chronic obstructive pulmonary disease (COPD), while their use for preparing a medicament for the treatment of bronchial asthma or COPD is particularly preferred according to the invention.

Also preferably, the medicament formulations according to the invention are used to prepare a medicament for the treatment of pulmonary emphysema which has its origins in COPD (chronic obstructive pulmonary disease) or al-proteinase inhibitor deficiency.

Also preferably, the medicament formulations according to the invention are used to prepare a medicament for the treatment of restrictive pulmonary diseases selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

Also preferably, the medicament formulations according to the invention are used to prepare a medicament for the treatment of interstitial pulmonary diseases selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic scleroderma or sarcoidosis, granulomatoses, such as for example Boeck's disease, idiopathic interstitial pneumonia or idiopathic pulmonary fibrosis (IPF).

Also preferably, the medicament formulations according to the invention are used to prepare a medicament for the treatment of cystic fibrosis or mucoviscidosis.

Also preferably, the medicament formulations according to the invention are used to prepare a medicament for the treatment of bronchitis, such as for example bronchitis caused by bacterial or viral infection, allergic bronchitis and toxic bronchitis.

Also preferably, the medicament formulations according to the invention are used to prepare a medicament for the treatment of bronchiectasis.

Also preferably, the medicament formulations according to the invention are used to prepare a medicament for the treatment of ARDS (adult respiratory distress syndrome).

Also preferably, the medicament formulations according to the invention are used to prepare a medicament for the treatment of pulmonary oedema, for example toxic pulmonary oedema after aspiration or inhalation of toxic substances and foreign substances.

Particularly preferably the present invention relates to the use of the medicament formulations according to the invention for preparing a medicament for the treatment of asthma or COPD. Also of particular importance is the above-mentioned use for preparing a medicament for treating inflammatory and obstructive respiratory complaints, most particularly asthma or COPD, several times a day, preferably three to four times a day.

The present invention also relates to a process for the treatment of the above-mentioned diseases, characterised in that one or more of the above-mentioned medicament formulations according to the invention are administered in therapeutically effective amounts.

The present invention further relates to the use of the above-mentioned medicament formulations for preparing a medicament for the treatment of one of the above-mentioned diseases, particularly asthma or COPD, characterised in that about 5 to 25 µl (microliters), preferably about 7 to 20 µl of the solutions according to the invention are administered per dose of medicament. It is particularly preferable to use the above-mentioned medicament formulations for preparing a medicament for the treatment of one of the above-mentioned diseases, particularly asthma or COPD, characterised in that about 10 to 13 µl of the solutions according to the invention are administered per dose of medicament.

It is particularly preferable to use the above-mentioned medicament formulations for preparing a medicament for the treatment of one of the above-mentioned diseases, particularly asthma or COPD, characterised in that the above-mentioned quantities of solution once or twice per dose are administered, while the administration of a single dose is particularly preferred according to the invention.

It is particularly preferable to use the above-mentioned medicament formulations for preparing a medicament for the treatment of one of the above-mentioned diseases, particularly asthma or COPD, characterised in that the above-mentioned administration of medicament occurring once or twice, preferably once per dose, is given at least once a day, preferably at least twice a day, particularly preferably three-to four times a day.

The present invention further relates to a method of treating one of the above-mentioned diseases, particularly asthma or COPD, characterised in that about 5 to 25 μl (microliters), preferably about 7 to 20 μl of the solutions according to the invention are administered per dose of medicament. Particularly preferred is a method of treating one of the above-mentioned diseases, particularly asthma or COPD, wherein about 10 to 13 μl of the solutions according to the invention are administered per dose of medicament.

Also particularly preferred is a method of treating one of the above-mentioned diseases, particularly asthma or COPD, characterised in that the above-mentioned quantities of solution are administered once or twice per dose, while it is particularly preferable to administer only one quantity per dose, according to the invention.

Also particularly preferred is a method of treating one of the above-mentioned diseases, particularly asthma or COPD, characterised in that the above-mentioned administration of medicament occurring once or twice, preferably once per dose, is given at least once a day, preferably at least twice a day, particularly preferably three to four times a day.

The formulations according to the invention may be inhaled orally or nasally. To achieve an optimum distribution of the active substances in the lungs it is advisable to use a liquid formulation free from propellant gases which is delivered using inhalers suitable for this purpose. A formulation of this kind may be administered by both oral and nasal inhalation. Those inhalers which are capable of nebulising a small amount of a liquid formulation in the dosage needed for therapeutic purposes within a few seconds into an aerosol suitable for therapeutic inhalation are particularly suitable.

An apparatus of this kind for the propellant-free administration of a metered amount of a liquid pharmaceutical composition for inhalation is described in detail for example in International Patent Application WO 91/14468 and also in WO 97/12687, cf. FIGS. 6a and 6b and the accompanying description. In a nebuliser of this kind a pharmaceutical solution is converted by means of a high pressure of up to 600 bar into an aerosol destined for the lungs, which is sprayed. Within the scope of the present specification reference is expressly made to the entire contents of the literature mentioned above.

In inhalers of this kind the formulations of solutions are stored in a reservoir. It is essential that the active substance formulations used are sufficiently stable when stored and at the same time are such that they can be administered directly, if possible without any further handling, in accordance with their medical purpose. Moreover, they must not contain any ingredients which might interact with the inhaler in such a way as to damage the inhaler or the pharmaceutical quality of the solution or of the aerosol produced.

To nebulise the solution a special nozzle is used as described for example in WO 94/07607 or WO 99/16530. Reference is expressly made here to both these publications.

The aim of the present invention is to provide an aqueous, ethanolic or aqueous-ethanolic formulation of the compound of formula 1 which meets the high standards needed in order to be able to achieve optimum nebulisation of a solution using the inhalers mentioned hereinbefore. The active substance formulations according to the invention must be of sufficiently high pharmaceutical quality, i.e. they should be pharmaceutically stable over a storage time of some years, preferably at least one year, more preferably two years.

These propellant-free formulations must also be capable of being nebulised under pressure using an inhaler, the composition delivered by the aerosol produced falling reproducibly within a specified range.

The medicament formulations according to the invention are preferably used in an inhaler of the kind described hereinbefore in order to produce the propellant-free aerosols according to the invention. At this point we should once again expressly mention the patent documents described hereinbefore, the contents of which are hereby incorporated by reference.

As described at the beginning, a further developed embodiment of the preferred inhaler is disclosed in WO 97/12687 (see in particular FIGS. 6a and 6b and the associated parts of the description). This nebuliser (Respimat®) can advantageously be used to produce the inhalable aerosols according to the invention. Because of its cylindrical shape and handy size of less than 9 to 15 cm long and 2 to 4 cm wide, the device can be carried anywhere by the patient. The nebuliser sprays a defined volume of the medicament formulation out through small nozzles at high pressures, so as to produce inhalable aerosols.

The preferred atomiser essentially consists of an upper housing part, a pump housing, a nozzle, a locking clamp, a spring housing, a spring and a storage container, characterised by a pump housing fixed in the upper housing part and carrying at one end a nozzle body with the nozzle or nozzle arrangement, a hollow piston with valve body, a power take-off flange in which the hollow body is fixed and which is located in the upper housing part, a locking clamping mechanism located in the upper housing part, a spring housing with the spring located therein, which is rotatably mounted on the upper housing part by means of a rotary bearing, a lower housing part which is fitted onto the spring housing in the axial direction.

The hollow piston with valve body corresponds to a device disclosed in WO 97/12687. It projects partially into the cylinder of the pump housing and is disposed to be axially movable in the cylinder. Reference is made particularly to FIGS. 1-4—especially FIG. 3—and the associated parts of the description. At the moment of release of the spring the hollow piston with valve body exerts, at its high pressure end, a pressure of 5 to 60 Mpa (about 50 to 600 bar), preferably 10 to 60 Mpa (about 100 to 600 bar) on the fluid, the measured amount of active substance solution. Volumes of 10 to 50 microliters are preferred, volumes of 10 to 20 microliters are more preferable, whilst a volume of 15 microliters per actuation is particularly preferred.

The valve body is preferably mounted at the end of the hollow piston which faces the nozzle body.

The nozzle in the nozzle body is preferably microstructured, i.e. manufactured by micro-engineering. Microstructured nozzle bodies are disclosed for example in WO-94/07607 and in WO 99/16530; reference is hereby made to the contents thereof, especially FIG. 1 of WO-94/07607 and the associated description.

The nozzle body consists for example of two sheets of glass and/or silicon securely fixed together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns and the length being 7 to 9 microns.

If there is a plurality of nozzle openings, preferably two, the directions of spraying of the nozzles in the nozzle body may run parallel to each other or may be inclined relative to one another in the direction of the nozzle opening. In the case of a nozzle body having at least two nozzle openings at the outlet end, the directions of spraying may be inclined relative to one another at an angle of 20 degrees to 160 degrees, preferably at an angle of 60 to 150 degrees, most preferably 80 to 100°.

The nozzle openings are preferably arranged at a spacing of 10 to 200 microns, more preferably at a spacing of 10 to 100 microns, still more preferably 30 to 70 microns. A spacing of 50 microns is most preferred.

The directions of spraying therefore meet in the region of the nozzle openings.

As already mentioned, the liquid pharmaceutical preparation hits the nozzle body at an entry pressure of up to 600 bar, preferably 200 to 300 bar and is atomised through the nozzle openings into an inhalable aerosol. The preferred particle sizes of the aerosol are up to 20 microns, preferably 3 to 10 microns.

The locking clamping mechanism contains a spring, preferably a cylindrical helical compression spring as a store for the mechanical energy. The spring acts on the power take-off flange as a spring member the movement of which is determined by the position of a locking member. The travel of the power take-off flange is precisely limited by an upper stop and a lower stop. The spring is preferably tensioned via a stepping-up gear, e.g. A helical sliding gear, by an external torque which is generated when the upper housing part is turned relative to the spring housing in the lower housing part. In this case, the upper housing part and the power take-off flange contain a single- or multi-speed spline gear.

The locking member with the engaging locking surfaces is arranged in an annular configuration around the power take-off flange. It consists for example of a ring of plastics or metal which is inherently radially elastically deformable. The ring is arranged in a plane perpendicular to the axis of the atomiser. After the locking of the spring, the locking surfaces of the locking member slide into the path of the power take-off flange and prevent the spring from being released. The locking member is actuated by means of a button. The actuating button is connected or coupled to the locking member. In order to actuate the locking clamping mechanism the actuating button is moved parallel to the annular plane, preferably into the atomiser, and the deformable ring is thereby deformed in the annular plane. Details of the construction of the locking clamping mechanism are described in WO 97/20590.

The lower housing part is pushed axially over the spring housing and covers the bearing, the drive for the spindle and the storage container for the fluid.

When the atomiser is operated, the upper part of the housing is rotated relative to the lower part, the lower part taking the spring housing with it. The spring meanwhile is compressed and biased by means of the helical sliding gear, and the clamping mechanism engages automatically. The angle of rotation is preferably a whole-number fraction of 360 degrees, e.g. 180 degrees. At the same time as the spring is tensioned, the power take-off component in the upper housing part is moved along by a given amount, the hollow piston is pulled back inside the cylinder in the pump housing, as a result of which some of the fluid from the storage container is sucked into the high pressure chamber in front of the nozzle.

If desired, a plurality of replaceable storage containers containing the fluid to be atomised can be inserted in the atomiser one after another and then used. The storage container contains the aqueous aerosol preparation according to the invention.

The atomising process is initiated by gently pressing the actuating button. The clamping mechanism then opens the way for the power take-off component. The biased spring pushes the piston into the cylinder in the pump housing. The fluid emerges from the nozzle of the atomiser in the form of a spray.

Further details of the construction are disclosed in PCT applications WO 97/12683 and WO 97/20590, to which reference is hereby made.

The components of the atomiser (nebuliser) are made of a material suitable for their function. The housing of the atomiser and—if the function allows—other parts as well are preferably made of plastics, e.g. by injection moulding. For medical applications, physiologically acceptable materials are used.

FIGS. 6 a/b of WO 97/12687 show the Respimat® nebuliser with which the aqueous aerosol preparations according to the invention can advantageously be inhaled.

FIG. 6 a shows a longitudinal section through the atomiser with the spring under tension, FIG. 6 b shows a longitudinal section through the atomiser with the spring released.

The upper housing part (51) contains the pump housing (52), on the end of which is mounted the holder (53) for the atomiser nozzle. In the holder is the nozzle body (54) and a filter (55). The hollow piston (57) fixed in the power take-off flange (56) of the locking clamping mechanism projects partly into the cylinder of the pump housing. At its end the hollow piston carries the valve body (58). The hollow piston is sealed off by the gasket (59). Inside the upper housing part is the stop (60) on which the power take-off flange rests when the spring is relaxed. Located on the power take-off flange is the stop (61) on which the power take-off flange rests when the spring is under tension. After the tensioning of the spring, the locking member (62) slides between the stop (61) and a support (63) in the upper housing part. The actuating button (64) is connected to the locking member. The upper housing part ends in the mouthpiece (65) and is closed off by the removable protective cap (66).

The spring housing (67) with compression spring (68) is rotatably mounted on the upper housing part by means of the snap-fit lugs (69) and rotary bearings. The lower housing part (70) is pushed over the spring housing. Inside the spring housing is the replaceable storage container (71) for the fluid (72) which is to be atomised. The storage container is closed off by the stopper (73), through which the hollow piston projects into the storage container and dips its end into the fluid (supply of active substance solution).

The spindle (74) for the mechanical counter is mounted on the outside of the spring housing. The drive pinion (75) is located at the end of the spindle facing the upper housing part. On the spindle is the slider (76).

The nebuliser described above is suitable for nebulising the aerosol preparations according to the invention to form an aerosol suitable for inhalation.

If the formulation according to the invention is nebulised using the method described above (Respimat®), the mass expelled, in at least 97%, preferably at least 98% of all the actuations of the inhaler (puffs), should correspond to a defined quantity with a range of tolerance of not more than 25%, preferably 20% of this quantity. Preferably, between 5 and 30 mg, more preferably between 5 and 20 mg of formulation are delivered as a defined mass per puff.

The formulation according to the invention can also be nebulised using inhalers other than those described above, for example jet-stream inhalers.

The present invention also relates to an inhalation kit consisting of one of the medicament preparations according to the invention described above and an inhaler suitable for nebulising this pharmaceutical preparation.

The present invention preferably relates to an inhalation kit consisting of one of the medicament preparations according to the invention described above and the Respimat® inhaler described above.

The examples of formulations given below serve as illustrations without restricting the subject matter of the present invention to the compositions shown by way of example.

The percentages given are percent by mass (w/w) in each case.

A) Preparation of the Formulations

Pure water is placed in a container and to this are added, with stirring, at ambient temperature, ipratropium bromide monohydrate, salbutamol sulphate, benzalkonium chloride (anhydrous) and disodium edetate-dihydrate. The quantities of ingredients used in each case are indicated by the formulation ingredients illustrated below. After all the ingredients have dissolved and water has been added if necessary to obtain the specified concentrations, the solution obtained is adjusted to a pH of 3.4 with 1N aqueous hydrochloric acid.

B) Examples of Formulations:

In the examples of formulations below, BAC denotes benzalkonium chloride and EDTA denotes disodium edetate-dihydrate. The Examples were adjusted to a pH of 3.4 with 1N aqueous hydrochloric acid.

| Example | BAC [mg/100 g] | EDTA [mg/100 g] | ipratropium bromide-monohydrate [g/100 g] | salbutamol [g/100 g] | purified water |
|---|---|---|---|---|---|
| 1 | 10 | 50 | 0.175 | 0.877[1] | ad 100 g |
| 2 | 10 | 10 | 0.175 | 0.877[1] | ad 100 g |
| 3 | 10 | 5 | 0.175 | 0.877[1] | ad 100 g |

[1] corresponds to 1.057 g salbutamol sulphate per 100 g solution;

C) Use in the Respimat:

If the formulations specified under B) are administered using the Respimat® inhaler, each puff (about 11.4 μl volume) delivers the quantities of formulation ingredients specified below to the patient.

| Example | BAC [mg/Hub] | EDTA [mg/Hub] | ipratropium bromide-monohydrate [mg/Hub] | salbutamol [mg/Hub] | purified water |
|---|---|---|---|---|---|
| 1 | 0.00114 | 0.0057 | 0.02 | 0.10[1] | ad 11.4 mg |
| 2 | 0.00114 | 0.00114 | 0.02 | 0.10[1] | ad 11.4 mg |
| 3 | 0.00114 | 0.00057 | 0.02 | 0.10[1] | ad 11.4 mg |

[1] corresponds to 0.1205 mg salbutamol sulphate per puff;

The invention claimed is:

1. A propellant-free solution formulation for inhalation which contain the active substances salbutamol, optionally in the form of the pharmacologically acceptable acid addition salts thereof, and ipratropium bromide and optionally further excipients, in a solvent selected from among water, ethanol and water-ethanol mixtures, the weight ratio of salbutamol to ipratropium bromide being in the range from 5:1 to 5.5:1, a preservative benzalkonium chloride and the solution formulation containing no other active substances, wherein the formulation contains as further constituents one or more complexing agents, wherein the solution comprises the one or more complexing agents in an amount of 3-7 mg per 100 grams of solution, and wherein a dose of the solution formulation is between about 5 μL and about 25 μL.

2. The propellant-free solution formulation according to claim 1, wherein the salbutamol is present in the form of one of the pharmacologically acceptable acid addition salts thereof with an acid selected from among hydrochloric acid, hydrobromic acid, nitric acid, sulphuric acid and phosphoric acid.

3. The propellant-free solution formulation according to claim 2, wherein the solvent is water.

4. The propellant-free solution formulation according to claim 1, wherein the pH of the formulation is in the range from 3.0 and 4.0.

5. The propellant-free solution formulation according to claim 4, wherein the pH is adjusted using inorganic or organic acids.

6. The propellant-free solution formulation according to claim 1, wherein the complexing agent is editic acid (EDTA) or one of the known salts thereof.

7. A propellant-free solution formulation according to claim 2, wherein the acid is sulphuric acid.

8. A propellant-free solution formulation according to claim 1, wherein the pH of the formulation is in the range from 3.1 and 3.7.

9. The propellant-free solution formulation according to claim 1, wherein the solution formulation is capable of treating at least one of asthma and chronic obstructive pulmonary disorder.

10. The propellant-free solution formulation according to claim 1, wherein a nebulizer is capable of converting the solution formulation into an aerosol at pressures up to 600 bar.

* * * * *